(12) United States Patent
Suedkamp et al.

(10) Patent No.: US 9,320,615 B2
(45) Date of Patent: Apr. 26, 2016

(54) DISTRACTIBLE INTERVERTEBRAL IMPLANT

(71) Applicant: DePuy Synthes Products, Inc., Raynham, MA (US)

(72) Inventors: Jann-Paul Suedkamp, Oberdorf (CH); Sean Saidha, Raynham, MA (US); Philipp Brun, Basel (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/143,529

(22) Filed: Dec. 30, 2013

(65) Prior Publication Data

US 2014/0114423 A1    Apr. 24, 2014

Related U.S. Application Data

(63) Continuation of application No. 13/170,557, filed on Jun. 28, 2011, now Pat. No. 8,623,091.

(60) Provisional application No. 61/359,554, filed on Jun. 29, 2010.

(51) Int. Cl.
*A61F 2/44*       (2006.01)
*A61B 17/86*    (2006.01)
(Continued)

(52) U.S. Cl.
CPC .............. *A61F 2/447* (2013.01); *A61F 2/4455* (2013.01); *A61B 17/86* (2013.01); *A61F 2002/2835* (2013.01); *A61F 2002/305* (2013.01); *A61F 2002/3008* (2013.01); *A61F 2002/3052* (2013.01); *A61F 2002/30387* (2013.01);
(Continued)

(58) Field of Classification Search
CPC ..................................................... A61F 2/4455
USPC ..................................................... 623/17.16
See application file for complete search history.

(56) References Cited

U.S. PATENT DOCUMENTS 3,867,728 A    2/1975  Stubstad et al.
4,349,921 A    9/1982  Kuntz
(Continued)

FOREIGN PATENT DOCUMENTS

CN    101909548 A    12/2010
DE    2804936           8/1979
(Continued)

OTHER PUBLICATIONS

U.S. Appl. No. 61/675,975, Jul. 26, 2012, Lechmann et al.
(Continued)

*Primary Examiner* — Ellen C Hammond
(74) *Attorney, Agent, or Firm* — Baker & Hostetler LLP

(57) ABSTRACT

A distractible intervertebral implant configured to be inserted in an insertion direction into an intervertebral space that is defined between a first vertebral body and a second vertebral body is disclosed. The implant may include a first body and a second body. The first body may define an outer surface that is configured to engage the first vertebral body, and an opposing inner surface that defines a rail. The second body may define an outer surface that is configured to engage the second vertebral body, and an inner surface that defines a recess configured to receive the rail of the first body. The second body moves in a vertical direction toward the second vertebral body as the second body is slid over the first body and the rail is received in the recess.

23 Claims, 9 Drawing Sheets

(51) Int. Cl.
*A61F 2/28* (2006.01)
*A61F 2/30* (2006.01)

(52) U.S. Cl.
CPC .............. *A61F2002/30433* (2013.01); *A61F 2002/30434* (2013.01); *A61F 2002/30472* (2013.01); *A61F 2002/30579* (2013.01); *A61F 2002/30604* (2013.01); *A61F 2002/30779* (2013.01); *A61F 2002/30787* (2013.01); *A61F 2002/30843* (2013.01); *A61F 2002/30845* (2013.01); *A61F 2002/4475* (2013.01); *A61F 2220/0025* (2013.01); *A61F 2220/0041* (2013.01); *A61F 2240/001* (2013.01); *A61F 2250/0008* (2013.01); *A61F 2250/0098* (2013.01); *A61F 2310/00017* (2013.01); *A61F 2310/00023* (2013.01); *A61F 2310/00041* (2013.01); *A61F 2310/00131* (2013.01); *A61F 2310/00179* (2013.01); *A61F 2310/00293* (2013.01); *A61F 2310/00796* (2013.01)

(56) References Cited

U.S. PATENT DOCUMENTS

| | | | |
|---|---|---|---|
| 4,759,766 A | | 7/1988 | Buettner-Janz et al. |
| 4,863,476 A | | 9/1989 | Shepperd |
| 5,059,193 A | | 10/1991 | Kuslich |
| 5,290,312 A | * | 3/1994 | Kojimoto et al. ......... 623/17.15 |
| 5,314,477 A | | 5/1994 | Marnay |
| 5,344,252 A | | 9/1994 | Kakimoto |
| 5,370,697 A | | 12/1994 | Baumgartner |
| 5,390,683 A | | 2/1995 | Pisharodi |
| 5,401,269 A | | 3/1995 | Buttner-Janz et al. |
| 5,425,773 A | | 6/1995 | Boyd et al. |
| 5,443,514 A | | 8/1995 | Steffee |
| 5,507,816 A | | 4/1996 | Bullivant |
| 5,522,899 A | | 6/1996 | Michelson |
| 5,534,029 A | | 7/1996 | Shima |
| 5,554,191 A | | 9/1996 | Lahille et al. |
| 5,556,431 A | | 9/1996 | Buttner-Janz |
| 5,562,738 A | | 10/1996 | Boyd et al. |
| 5,609,635 A | | 3/1997 | Michelson |
| 5,653,763 A | | 8/1997 | Errico |
| 5,658,335 A | | 8/1997 | Allen |
| 5,665,122 A | | 9/1997 | Kambin |
| 5,676,701 A | | 10/1997 | Yuan et al. |
| 5,683,465 A | | 11/1997 | Shinn et al. |
| 5,697,977 A | | 12/1997 | Pisharodi |
| 5,716,415 A | | 2/1998 | Steffee |
| 5,772,661 A | | 6/1998 | Michelson |
| 5,782,832 A | | 7/1998 | Larsen et al. |
| 5,860,973 A | | 1/1999 | Michelson |
| 5,865,848 A | | 2/1999 | Baker |
| 5,888,224 A | | 3/1999 | Beckers et al. |
| 5,888,226 A | | 3/1999 | Rogozinski |
| 5,893,889 A | | 4/1999 | Harrington |
| 5,893,890 A | | 4/1999 | Pisharodi |
| 5,980,522 A | | 11/1999 | Koros et al. |
| 5,989,291 A | | 11/1999 | Ralph et al. |
| 6,039,761 A | | 3/2000 | Li |
| 6,039,763 A | | 3/2000 | Shelokov |
| 6,045,579 A | | 4/2000 | Hochshuler |
| 6,102,950 A | | 8/2000 | Vaccaro |
| 6,106,557 A | | 8/2000 | Robioneck et al. |
| 6,113,637 A | | 9/2000 | Gill et al. |
| 6,113,638 A | | 9/2000 | Williams |
| 6,117,174 A | | 9/2000 | Nolan |
| 6,127,597 A | | 10/2000 | Beyar et al. |
| 6,129,763 A | | 10/2000 | Chauvin et al. |
| 6,146,387 A | | 11/2000 | Trott et al. |
| 6,176,882 B1 | | 1/2001 | Biedermann et al. |
| 6,179,794 B1 | | 1/2001 | Burras |
| 6,179,873 B1 | | 1/2001 | Zientek |
| 6,183,517 B1 | | 2/2001 | Suddaby |
| 6,193,757 B1 | | 2/2001 | Foley et al. |
| 6,296,647 B1 | | 10/2001 | Robioneck et al. |
| 6,302,914 B1 | | 10/2001 | Michelson |
| 6,332,895 B1 | | 12/2001 | Suddaby |
| 6,368,350 B1 | | 4/2002 | Erickson et al. |
| 6,368,351 B1 | | 4/2002 | Glenn |
| 6,375,682 B1 | | 4/2002 | Fleischmann et al. |
| 6,387,130 B1 | | 5/2002 | Stone |
| 6,409,766 B1 | | 6/2002 | Brett |
| 6,419,705 B1 | | 7/2002 | Erickson |
| 6,419,706 B1 | | 7/2002 | Graf |
| 6,436,140 B1 | | 8/2002 | Liu et al. |
| 6,454,806 B1 | | 9/2002 | Cohen et al. |
| 6,454,807 B1 | | 9/2002 | Jackson |
| 6,468,310 B1 | | 10/2002 | Ralph et al. |
| 6,488,710 B2 | | 12/2002 | Besselink |
| 6,517,580 B1 | | 2/2003 | Ramadan et al. |
| 6,527,804 B1 | | 3/2003 | Gauchet et al. |
| 6,558,424 B2 | | 5/2003 | Thalgott |
| 6,562,074 B2 | | 5/2003 | Gerbec et al. |
| 6,582,468 B2 | | 6/2003 | Gauchet |
| 6,610,094 B2 | | 8/2003 | Husson |
| 6,641,614 B1 | | 11/2003 | Wagner et al. |
| 6,648,917 B2 | | 11/2003 | Gerbec et al. |
| 6,676,665 B2 | | 1/2004 | Foley et al. |
| 6,706,070 B1 | | 3/2004 | Wagner et al. |
| 6,719,796 B2 | | 4/2004 | Cohen et al. |
| 6,723,126 B1 | | 4/2004 | Berry |
| 6,733,532 B1 | | 5/2004 | Gauchet et al. |
| 6,740,117 B2 | | 5/2004 | Ralph et al. |
| 6,743,255 B2 | | 6/2004 | Ferree |
| 6,793,678 B2 | | 9/2004 | Hawkins |
| 6,805,714 B2 | | 10/2004 | Sutcliffe |
| 6,852,129 B2 | | 2/2005 | Gerbec et al. |
| 6,855,167 B2 | | 2/2005 | Shimp |
| 6,863,673 B2 | | 3/2005 | Gerbec et al. |
| 6,881,229 B2 | | 4/2005 | Khandler |
| 6,893,464 B2 | | 5/2005 | Kiester |
| 6,936,071 B1 | | 8/2005 | Marnay et al. |
| 6,953,477 B2 | | 10/2005 | Berry |
| 6,955,691 B2 | | 10/2005 | Chae et al. |
| 6,969,404 B2 | | 11/2005 | Ferree |
| 6,969,405 B2 | | 11/2005 | Suddaby |
| 7,018,412 B2 | | 3/2006 | Ferreira et al. |
| 7,018,416 B2 | | 3/2006 | Hanson et al. |
| 7,037,339 B2 | | 5/2006 | Houfburg et al. |
| 7,083,650 B2 | | 8/2006 | Moskowitz et al. |
| 7,094,257 B2 | | 8/2006 | Mujwid et al. |
| 7,156,876 B2 | | 1/2007 | Moumene et al. |
| 7,211,112 B2 | | 5/2007 | Baynham et al. |
| 7,217,293 B2 | | 5/2007 | Branch |
| 7,220,280 B2 | | 5/2007 | Kast et al. |
| 7,223,292 B2 | | 5/2007 | Messerli et al. |
| 7,226,483 B2 | | 6/2007 | Gerber et al. |
| 7,235,101 B2 | | 6/2007 | Berry et al. |
| 7,326,248 B2 | | 2/2008 | Michelson |
| 7,503,933 B2 | | 3/2009 | Michelson |
| 7,507,241 B2 | | 3/2009 | Levy et al. |
| 7,517,363 B2 | | 4/2009 | Rogers |
| 7,569,074 B2 | | 8/2009 | Eiserman et al. |
| 7,618,458 B2 | | 11/2009 | Biedermann et al. |
| 7,621,950 B1 | | 11/2009 | Globerman et al. |
| 7,621,960 B2 | | 11/2009 | Boyd et al. |
| 7,691,147 B2 | | 4/2010 | Gutlin et al. |
| 7,703,727 B2 | | 4/2010 | Selness |
| 7,722,612 B2 | | 5/2010 | Sala et al. |
| 7,722,674 B1 | | 5/2010 | Grotz |
| 7,749,270 B2 | | 7/2010 | Peterman |
| 7,771,473 B2 | | 8/2010 | Thramann |
| 7,785,368 B2 | | 8/2010 | Schaller |
| 7,789,914 B2 | | 9/2010 | Michelson |
| 7,819,921 B2 | | 10/2010 | Grotz |
| 7,824,445 B2 | | 11/2010 | Biro et al. |
| 7,837,734 B2 | | 11/2010 | Zucherman et al. |
| 7,846,206 B2 | | 12/2010 | Oglaza et al. |
| 7,850,733 B2 | | 12/2010 | Baynham et al. |
| 7,854,766 B2 | | 12/2010 | Moskowitz et al. |
| 7,874,980 B2 | | 1/2011 | Sonnenschein et al. |

(56) References Cited

U.S. PATENT DOCUMENTS

| | | |
|---|---|---|
| 7,879,098 B1 | 2/2011 | Simmons |
| 7,887,589 B2 | 2/2011 | Glenn et al. |
| 7,909,870 B2 | 3/2011 | Kraus |
| 7,922,729 B2 | 4/2011 | Michelson |
| 7,951,199 B2 | 5/2011 | Miller |
| 7,985,231 B2 | 7/2011 | Sankaran |
| 7,993,403 B2 | 8/2011 | Foley et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,062,375 B2 | 11/2011 | Glerum et al. |
| 8,075,621 B2 | 12/2011 | Michelson |
| 8,128,700 B2 | 3/2012 | Delurio et al. |
| 8,177,812 B2 | 5/2012 | Sankaran |
| 8,192,495 B2 | 6/2012 | Simpson et al. |
| 8,221,501 B2 | 7/2012 | Eiserman et al. |
| 8,221,502 B2 | 7/2012 | Branch |
| 8,231,681 B2 | 7/2012 | Castleman et al. |
| 8,236,058 B2 | 8/2012 | Fabian et al. |
| 8,241,358 B2 | 8/2012 | Butler et al. |
| 8,257,442 B2 | 9/2012 | Edie et al. |
| 8,267,939 B2 | 9/2012 | Cipoletti et al. |
| 8,273,128 B2 | 9/2012 | Oh et al. |
| 8,287,599 B2 | 10/2012 | McGuckin |
| 8,303,663 B2 | 11/2012 | Jimenez et al. |
| 8,323,345 B2 | 12/2012 | Sledge |
| 8,328,852 B2 | 12/2012 | Zehavi et al. |
| 8,337,559 B2 | 12/2012 | Hansell et al. |
| 8,353,961 B2 | 1/2013 | McClintock |
| 8,382,842 B2 | 2/2013 | Greenhalgh et al. |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller |
| 8,486,148 B2 | 7/2013 | Butler et al. |
| 8,491,659 B2 | 7/2013 | Weiman |
| 8,506,635 B2 | 8/2013 | Palmatier et al. |
| 8,518,087 B2 | 8/2013 | Morgenstern et al. |
| 8,518,120 B2 | 8/2013 | Glerum et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim et al. |
| 8,591,585 B2 | 11/2013 | McLaughlin et al. |
| 8,603,170 B2 | 12/2013 | Cipoletti et al. |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 * | 12/2014 | Hawkins et al. .......... 623/17.16 |
| 8,926,704 B2 | 1/2015 | Glerum et al. |
| 8,936,641 B2 | 1/2015 | Cain |
| 8,940,052 B2 | 1/2015 | Lechmann et al. |
| 8,986,387 B1 | 3/2015 | To et al. |
| 9,005,291 B2 | 4/2015 | Loebl et al. |
| 9,039,767 B2 | 5/2015 | Raymond et al. |
| 9,039,771 B2 | 5/2015 | Glerum et al. |
| 9,060,876 B1 | 6/2015 | To et al. |
| 9,078,767 B1 | 7/2015 | McLean |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,107,766 B1 | 8/2015 | Mclean et al. |
| 2002/0010070 A1 | 1/2002 | Cales et al. |
| 2002/0068976 A1 | 6/2002 | Jackson |
| 2002/0068977 A1 | 6/2002 | Jackson |
| 2002/0128715 A1 | 9/2002 | Bryan et al. |
| 2002/0128716 A1 | 9/2002 | Cohen et al. |
| 2002/0151976 A1 | 10/2002 | Foley et al. |
| 2002/0165612 A1 | 11/2002 | Gerber et al. |
| 2003/0004575 A1 | 1/2003 | Erickson |
| 2003/0004576 A1 | 1/2003 | Thalgott |
| 2003/0023305 A1 | 1/2003 | McKay |
| 2003/0040799 A1 | 2/2003 | Boyd et al. |
| 2003/0065396 A1 | 4/2003 | Michelson |
| 2003/0078667 A1 | 4/2003 | Manasas et al. |
| 2003/0130739 A1 | 7/2003 | Gerbec et al. |
| 2003/0135275 A1 | 7/2003 | Garcia |
| 2003/0139812 A1 | 7/2003 | Garcia |
| 2003/0139813 A1 | 7/2003 | Messerli et al. |
| 2003/0233145 A1 | 12/2003 | Landry et al. |
| 2004/0030387 A1 | 2/2004 | Landry et al. |
| 2004/0064144 A1 | 4/2004 | Johnson et al. |
| 2004/0087947 A1 | 5/2004 | Lim |
| 2004/0088055 A1 | 5/2004 | Hanson et al. |
| 2004/0127991 A1 | 7/2004 | Ferree |
| 2004/0153065 A1 | 8/2004 | Lim |
| 2004/0153156 A1 | 8/2004 | Cohen et al. |
| 2004/0162618 A1 | 8/2004 | Mujwid et al. |
| 2004/0172133 A1 | 9/2004 | Gerber et al. |
| 2004/0186570 A1 | 9/2004 | Rapp |
| 2004/0186577 A1 | 9/2004 | Ferree |
| 2004/0230309 A1 | 11/2004 | DiMauro |
| 2005/0038515 A1 | 2/2005 | Kunzler |
| 2005/0113916 A1 | 5/2005 | Branch |
| 2005/0113917 A1 | 5/2005 | Chae et al. |
| 2005/0125062 A1 | 6/2005 | Biedermann et al. |
| 2005/0177235 A1 | 8/2005 | Baynham et al. |
| 2005/0222681 A1 | 10/2005 | Richley et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2006/0058876 A1 | 3/2006 | McKinley |
| 2006/0100706 A1 | 5/2006 | Shadduck et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142858 A1 | 6/2006 | Colleran et al. |
| 2006/0206207 A1 | 9/2006 | Dryer et al. |
| 2006/0235531 A1 | 10/2006 | Buettner |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2007/0010886 A1 | 1/2007 | Banick et al. |
| 2007/0055377 A1 | 3/2007 | Hanson et al. |
| 2007/0118222 A1 | 5/2007 | Lang |
| 2007/0149978 A1 | 6/2007 | Shezifi et al. |
| 2007/0173939 A1 | 7/2007 | Kim et al. |
| 2007/0191959 A1 | 8/2007 | Hartmann et al. |
| 2007/0198089 A1 | 8/2007 | Moskowitz et al. |
| 2007/0208423 A1 | 9/2007 | Messerli et al. |
| 2007/0219634 A1 | 9/2007 | Greenhalgh et al. |
| 2007/0233244 A1 | 10/2007 | Lopez et al. |
| 2007/0270968 A1 | 11/2007 | Baynham et al. |
| 2007/0276375 A1 | 11/2007 | Rapp |
| 2007/0299521 A1 | 12/2007 | Glenn |
| 2008/0009877 A1 | 1/2008 | Sankaran et al. |
| 2008/0015701 A1 | 1/2008 | Garcia et al. |

(56) References Cited

U.S. PATENT DOCUMENTS

| | | |
|---|---|---|
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058944 A1 | 3/2008 | Duplessis et al. |
| 2008/0065219 A1 | 3/2008 | Dye |
| 2008/0082173 A1 | 4/2008 | Delurio et al. |
| 2008/0140207 A1 | 6/2008 | Olmos |
| 2008/0147193 A1 | 6/2008 | Matthis et al. |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0243251 A1 | 10/2008 | Stad et al. |
| 2008/0243254 A1 | 10/2008 | Butler |
| 2008/0249622 A1 | 10/2008 | Gray |
| 2008/0281425 A1 | 11/2008 | Thalgott |
| 2009/0005870 A1* | 1/2009 | Hawkins et al. .......... 623/17.11 |
| 2009/0005873 A1 | 1/2009 | Slivka et al. |
| 2009/0030423 A1 | 1/2009 | Puno |
| 2009/0054991 A1 | 2/2009 | Biyani |
| 2009/0076610 A1 | 3/2009 | Afzal |
| 2009/0099568 A1 | 4/2009 | Lowry et al. |
| 2009/0112320 A1 | 4/2009 | Kraus |
| 2009/0112324 A1 | 4/2009 | Refai et al. |
| 2009/0177284 A1 | 7/2009 | Rogers et al. |
| 2009/0222096 A1 | 9/2009 | Trieu |
| 2009/0222099 A1 | 9/2009 | Liu et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0292361 A1 | 11/2009 | Lopez et al. |
| 2010/0016905 A1 | 1/2010 | Greenhalgh et al. |
| 2010/0179594 A1 | 7/2010 | Theofilos et al. |
| 2010/0204795 A1 | 8/2010 | Greenhalgh |
| 2010/0234956 A1 | 9/2010 | Attia et al. |
| 2010/0262240 A1 | 10/2010 | Chavatte et al. |
| 2010/0286783 A1 | 11/2010 | Lechmann et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0093074 A1 | 4/2011 | Glerum et al. |
| 2011/0130835 A1 | 6/2011 | Ashley et al. |
| 2011/0130838 A1 | 6/2011 | Morgenstern et al. |
| 2011/0144753 A1 | 6/2011 | Marchek et al. |
| 2011/0172716 A1 | 7/2011 | Glerum |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0185049 A1 | 7/2012 | Varela |
| 2012/0197403 A1 | 8/2012 | Merves |
| 2012/0197405 A1 | 8/2012 | Cuevas et al. |
| 2012/0226357 A1 | 9/2012 | Varela |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2013/0030536 A1 | 1/2013 | Rhoda et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2014/0025169 A1 | 1/2014 | Lechmann et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0228959 A1 | 8/2014 | Niemiec et al. |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0277474 A1 | 9/2014 | Robinson et al. |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2015/0012097 A1 | 1/2015 | Ibarra et al. |
| 2015/0045894 A1 | 2/2015 | Hawkins et al. |
| 2015/0094812 A1 | 4/2015 | Marden et al. |
| 2015/0094813 A1 | 4/2015 | Lechmann et al. |
| 2015/0112438 A1 | 4/2015 | McLean |
| 2015/0182347 A1 | 7/2015 | Robinson |
| 2015/0250606 A1 | 9/2015 | Mclean |

FOREIGN PATENT DOCUMENTS

| | | |
|---|---|---|
| DE | 3911610 | 10/1990 |
| DE | 4012622 | 7/1997 |
| DE | 202008001079 | 3/2008 |
| EP | 282161 | 9/1988 |
| EP | 678489 | 10/1995 |
| EP | 1290985 | 3/2003 |
| EP | 1532949 | 5/2005 |
| EP | 1541096 | 6/2005 |
| EP | 1541096 A1 | 6/2005 |
| EP | 1683593 | 7/2006 |
| EP | 1698305 B1 | 8/2007 |
| EP | 1843723 B1 | 3/2010 |
| EP | 2368529 | 9/2011 |
| EP | 2237748 B1 | 9/2012 |
| EP | 2764851 | 8/2014 |
| FR | 2730159 | 8/1996 |
| FR | 2874814 A1 | 3/2006 |
| FR | 2718635 | 12/2015 |
| JP | 2003-526457 | 9/2003 |
| JP | 2006-516456 | 7/2006 |
| JP | 2007-54666 | 3/2007 |
| JP | 2011-509766 A | 3/2011 |
| WO | WO 94/04100 | 3/1994 |
| WO | WO 95/31158 | 11/1995 |
| WO | WO 97/00054 | 1/1997 |
| WO | WO 99/53871 | 10/1999 |
| WO | WO 00/12033 | 3/2000 |
| WO | WO 00/74605 | 12/2000 |
| WO | WO 01/01893 | 1/2001 |
| WO | WO 01/01895 | 1/2001 |
| WO | WO 01/17464 | 3/2001 |
| WO | WO 2005/112834 | 12/2005 |

(56) References Cited

FOREIGN PATENT DOCUMENTS

| | | |
|---|---|---|
| WO | WO 2006/047587 | 5/2006 |
| WO | WO 2006/058281 | 6/2006 |
| WO | WO 2006/065419 | 6/2006 |
| WO | WO 2006/081843 | 8/2006 |
| WO | WO 2007/028098 | 3/2007 |
| WO | WO 2007/048012 A2 | 4/2007 |
| WO | WO 2008/044057 | 4/2008 |
| WO | WO 2007/009107 | 8/2008 |
| WO | WO 2009/092102 | 7/2009 |
| WO | WO 2009/064787 | 8/2009 |
| WO | WO 2009/124269 | 10/2009 |
| WO | WO 2009/143496 | 11/2009 |
| WO | WO 2010/068725 | 6/2010 |
| WO | WO 2010/148112 | 12/2010 |
| WO | WO 2011/142761 | 11/2011 |
| WO | WO 2012/009152 | 1/2012 |
| WO | WO 2012/089317 | 7/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 5/2013 |
| WO | WO 2013/062903 | 5/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |
| WO | WO 2014/144696 | 9/2014 |

OTHER PUBLICATIONS

U.S. Appl. No. 14/685,358, Apr. 13, 2015, Marden et al.
U.S. Appl. No. 14/640,220, Mar. 6, 2015, Marden.
U.S. Appl. No. 14/685,402, Apr. 13, 2015, Cain.
U.S. Appl. No. 14/790,866, Jul. 2, 2015, Thommen et al.
International Patent Application No. PCT/US2013/029014, International Search Report dated Jul. 1, 2013, 7 pages.
Chiang, Biomechanical Comparison of Instrumented Posterior Lumbar Interbody Fusion with One or Two Cages by Finite Element Analysis, Spine, 2006, pp. E682-E689, vol. 31(19), Lippincott Williams & Wilkins, Inc.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hunt, Expanable cage placement via a posterolateral approach in lumbar spine reconstructions, Journal of Neurosurgery: Spine, 2006, pp. 271-274, vol. 5.
Krbec, [Replacement of the vertebral body with an expansion implant (Synex)], Acta Chir Orthop Traumatol Cech, 2002, pp. 158-162, vol. 69(3).
Polikeit, The importance of the endplate for interbody cages in the lumbar spine, Eur Spine J, 2003, pp. 556-561, vol. 12.
Shin, Posterior Lumbar Interbody Fusion via a Unilateral Approach, Yonsei Medical Journal, 2006, pp. 319-325, vol. 47(3).
European Search Report EP03253921 dated Nov. 13, 2003; 4 pages.
Hoogland, T. et al., Total Lumbar Intervertebral Disc Replacement: testing of a New Articulating Space in Human Cadaver Spines—24th Annual ORS, Dallas TX, Feb. 21-23, 1978, 8 pages.

* cited by examiner

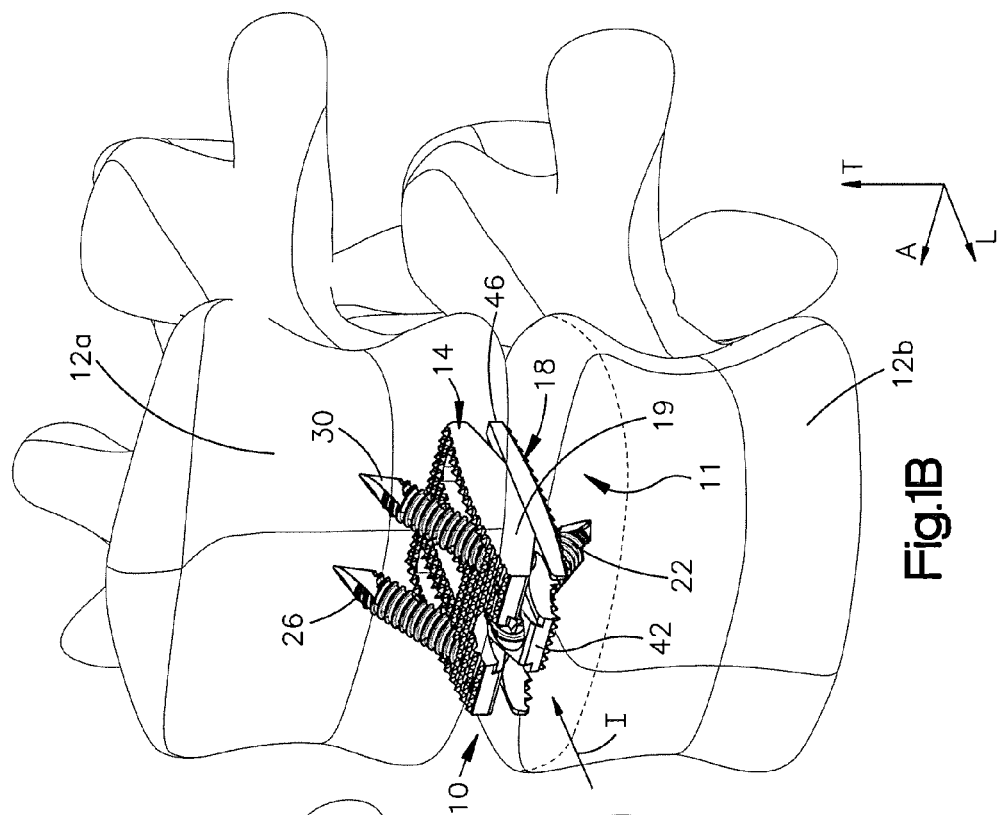
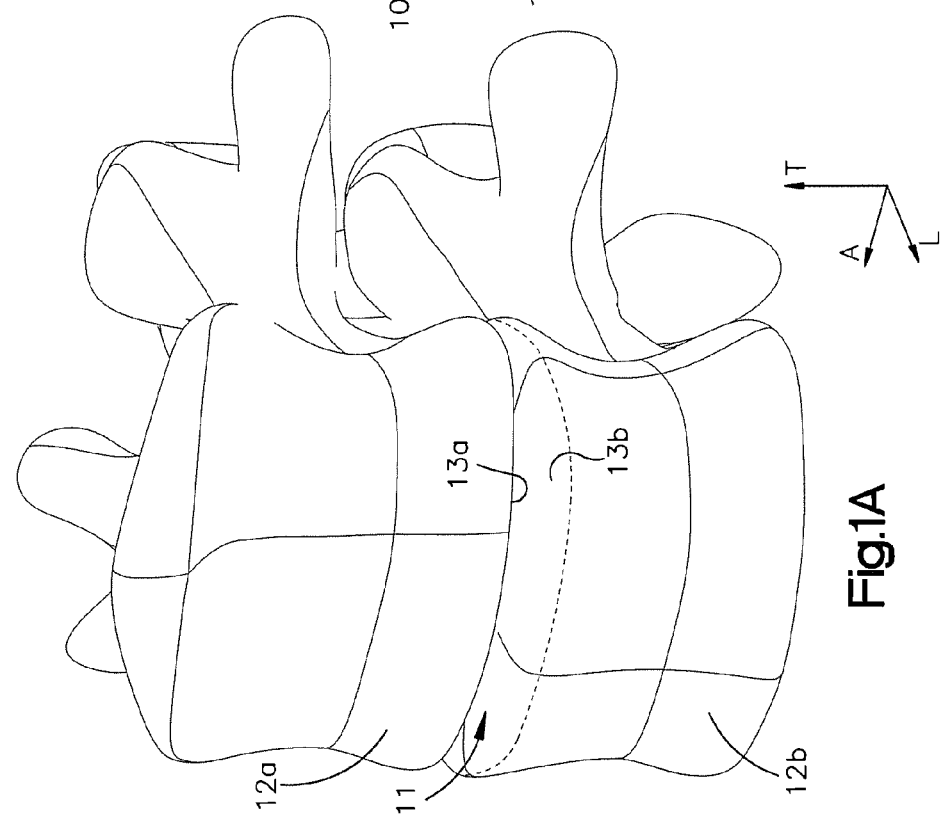
Fig.1A
Fig.1B

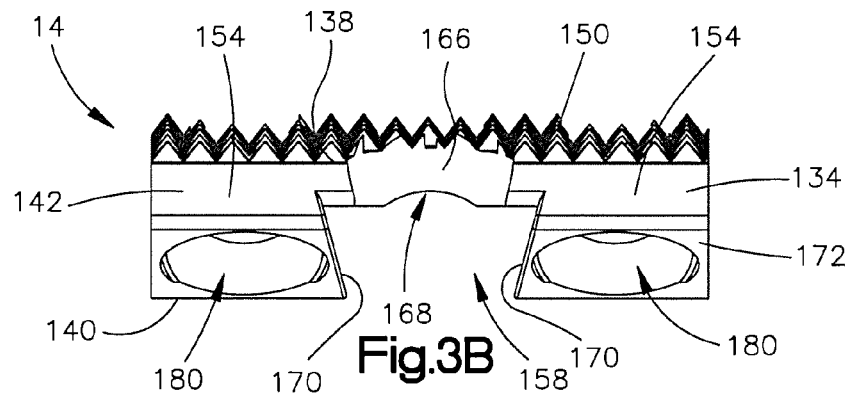
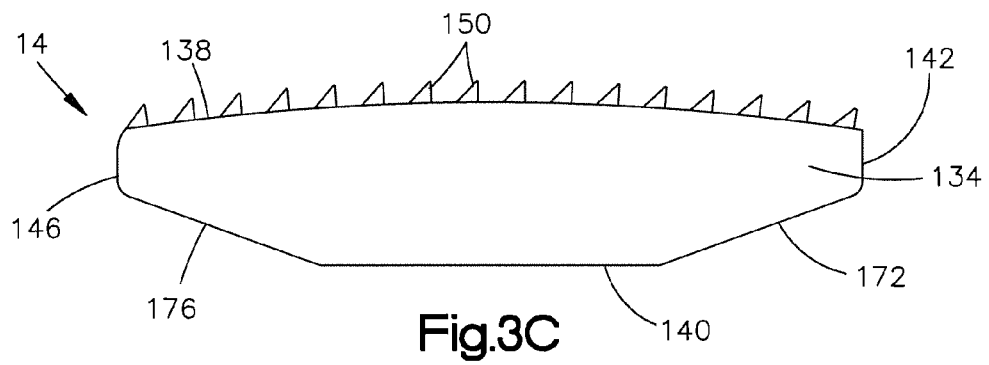
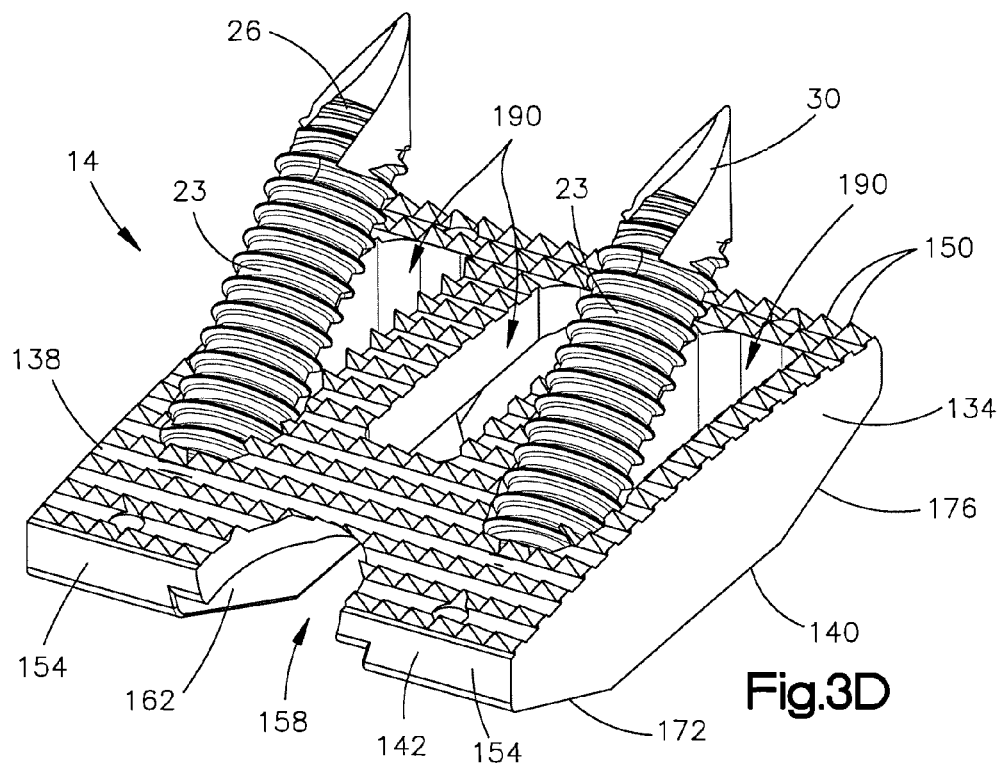

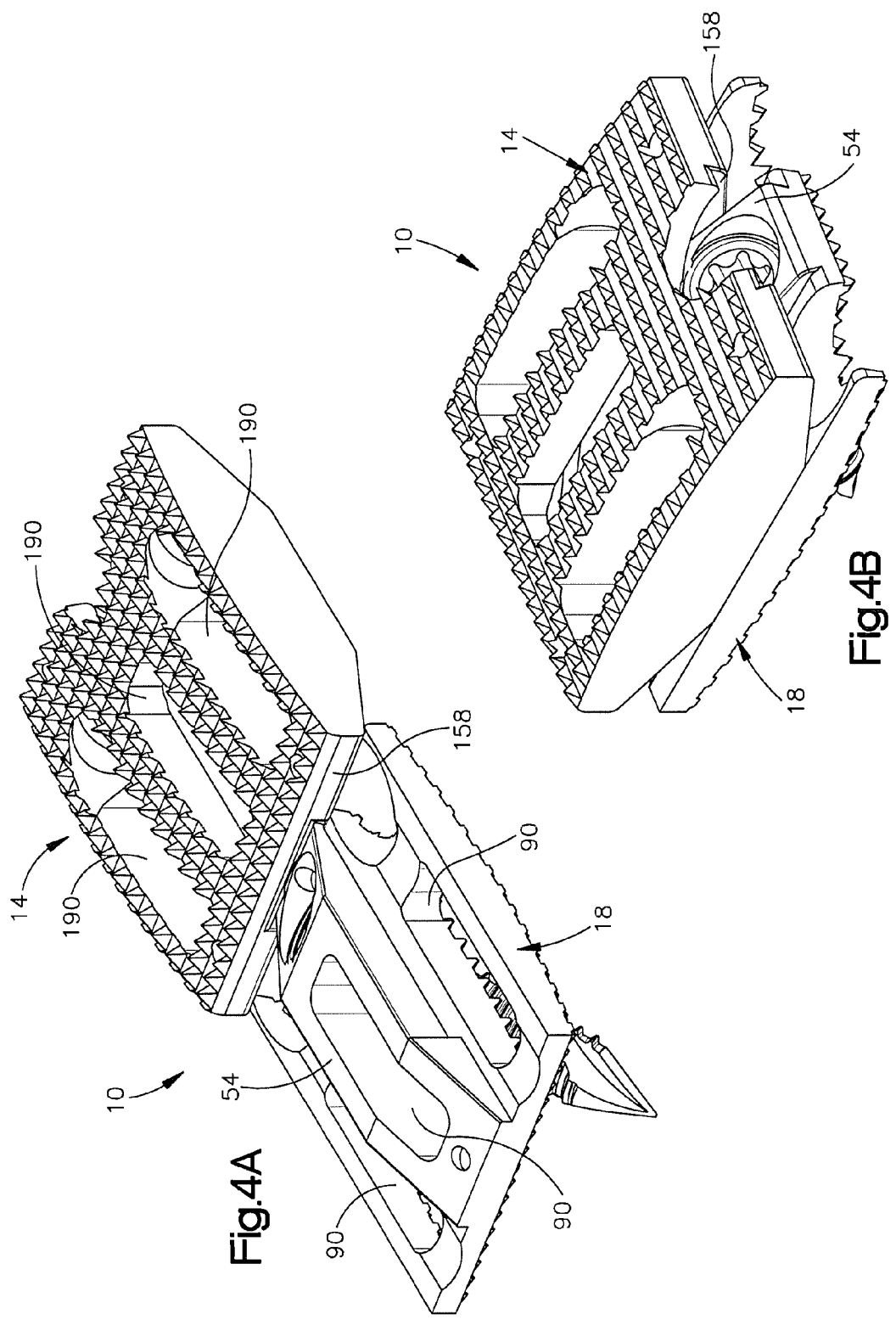

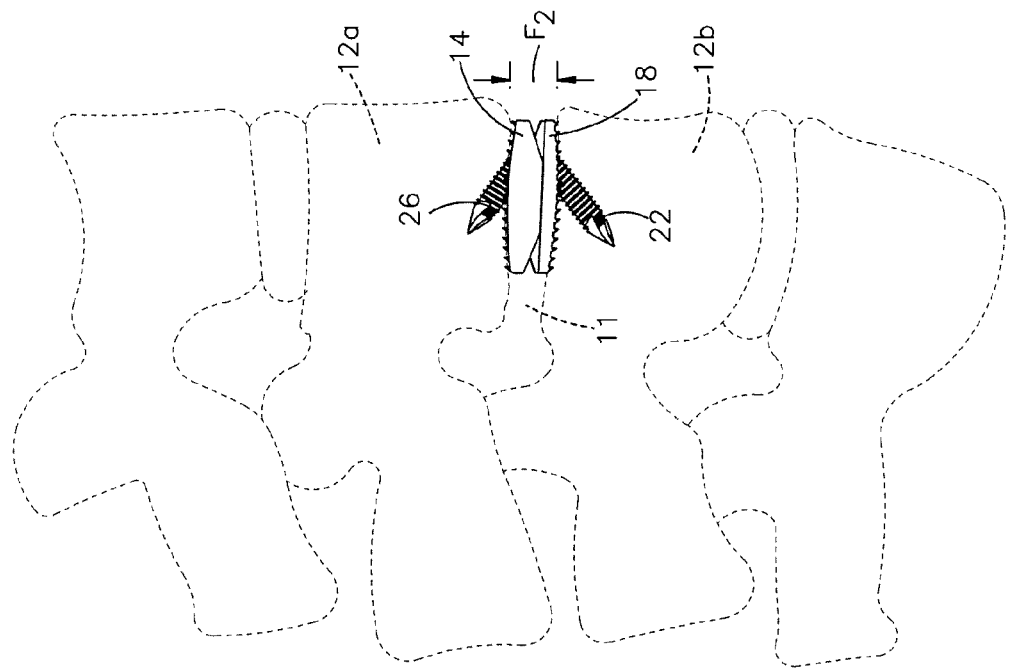
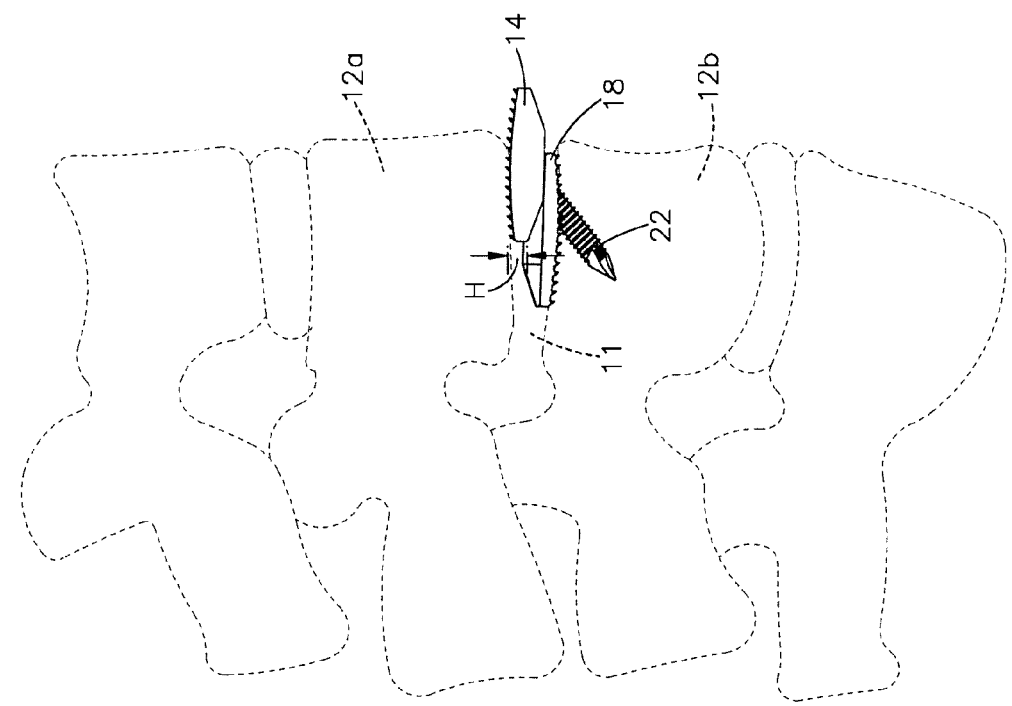

DISTRACTIBLE INTERVERTEBRAL IMPLANT

CROSS REFERENCE TO RELATED APPLICATIONS

This application is a continuation of U.S. patent application Ser. No. 13/170,557, filed Jun. 28, 2011 which claims the benefit of U.S. Provision Application Ser. No. 61/359,554 filed Jun. 29, 2010, the contents of each of which are hereby incorporated by reference in their entirety, herein.

BACKGROUND

Historically, after complete removal of a disc from between adjacent vertebrae, the adjacent vertebrae were fused together. This "spinal fusion" procedure, which is still in use today, is a widely accepted surgical treatment for symptomatic lumbar and cervical degenerative disc disease. More recently, disc arthoplasty may be utilized to insert an artificial intervertebral disc implant into the intervertebral space between adjacent vertebrae. Such a disc implant allows limited universal movement of the adjacent vertebrae with respect to each other. The aim of total disc replacement is to remove pain generation (caused by a degenerated disc), restore anatomy (disc height), and maintain mobility in the functional spinal unit so that the spine remains in an adapted sagittal balance. Sagittal balance is defined as the equilibrium of the trunk with the legs and pelvis to maintain harmonious sagittal curves and thus the damping effect of the spine. In contrast with fusion techniques, total disc replacement preserves mobility in the motion segment and attempts to mimic physiologic conditions.

SUMMARY

A distractible intervertebral implant configured to be inserted in an insertion direction into an intervertebral space that is defined between a first vertebral body and a second vertebral body is disclosed. The implant may include a first implant body and a second implant body. The first implant body may define an outer surface that is configured to face the first vertebral body, and an opposing inner surface that defines a rail. The second implant body may define an outer surface that is configured to face the second vertebral body, and an inner surface that defines a recess configured to receive the rail of the first implant body. The second implant body is configured to move along the vertical direction as the second implant body is translated over the first implant body and the rail is received by the recess, so as to distract the first and second vertebral bodies.

In another embodiment, the implant may include a first implant body and a second implant body. The first implant body may include a pair of first side regions, and may define an outer surface that is configured to face the first vertebral body. The second implant body may also include a pair of second side regions. Each second side region may have an anterior end that angles toward the first implant body as the anterior end extends in a direction opposite the insertion direction. The second implant body may define an outer surface that is configured to face the second vertebral body. The anterior ends of the second implant body are configured to contact the first side regions of the first implant body as the second implant body is translated over the first implant body to thereby cause the outer surface of the second implant body to move away from the outer surface of the first implant body.

In another embodiment, a method for inserting an intervertebral implant into an intervertebral disc space defined between first and second vertebral bodies is disclosed. The method may include the step of inserting a first implant body into the intervertebral space such that as the first implant body is being inserted at least one of the first and second vertebral bodies moves away from the other vertebral body. The first implant body may include an outer surface that faces the first vertebral body, and an inner surface. The method may further include inserting a second implant body into the intervertebral space by sliding the second implant body over the inner surface of the first implant body. The second implant body may cause at least one of the first and second vertebral bodies to move away from the other as the second implant body is being inserted. The second implant body may include an outer surface that faces the second vertebral body.

BRIEF DESCRIPTION OF THE DRAWINGS

The foregoing summary, as well as the following detailed description of a preferred embodiment of the application, will be better understood when read in conjunction with the appended drawings. For the purposes of illustrating the distractable fusion implant and related instruments of the present application, there is shown in the drawings a preferred embodiment. It should be understood, however, that the application is not limited to the precise arrangements and instrumentalities shown. In the drawings:

FIG. 1A is a front perspective view of an intervertebral space defined between a superior vertebral body and an inferior vertebral body;

FIG. 1B is a front perspective view of a distractible intervertebral implant inserted into the intervertebral space, the implant including an inferior implant body and a superior implant body;

FIG. 3B is a front elevation view of the superior implant body shown in FIG. 3A;

FIG. 3C is a side elevation view of the superior implant body shown in FIG. 3A;

FIG. 3D is a front perspective view of the superior implant body shown in FIG. 3A with a pair of locking screws being inserted into a pair of bores of the superior implant body;

FIG. 4A is a back perspective view of the superior implant body being slid onto the inferior implant body;

FIG. 4B is a front perspective view of the superior implant body fully slid onto the inferior implant body to define the distractible fusion implant;

FIG. 5C is a side elevation view of the superior implant body further slid over the inferior implant body within the intervertebral space; and FIG. 5D is a side elevational view of the superior implant body affixed to the superior vertebral body with second and third locking screws.

DETAILED DESCRIPTION

Figure 2A:
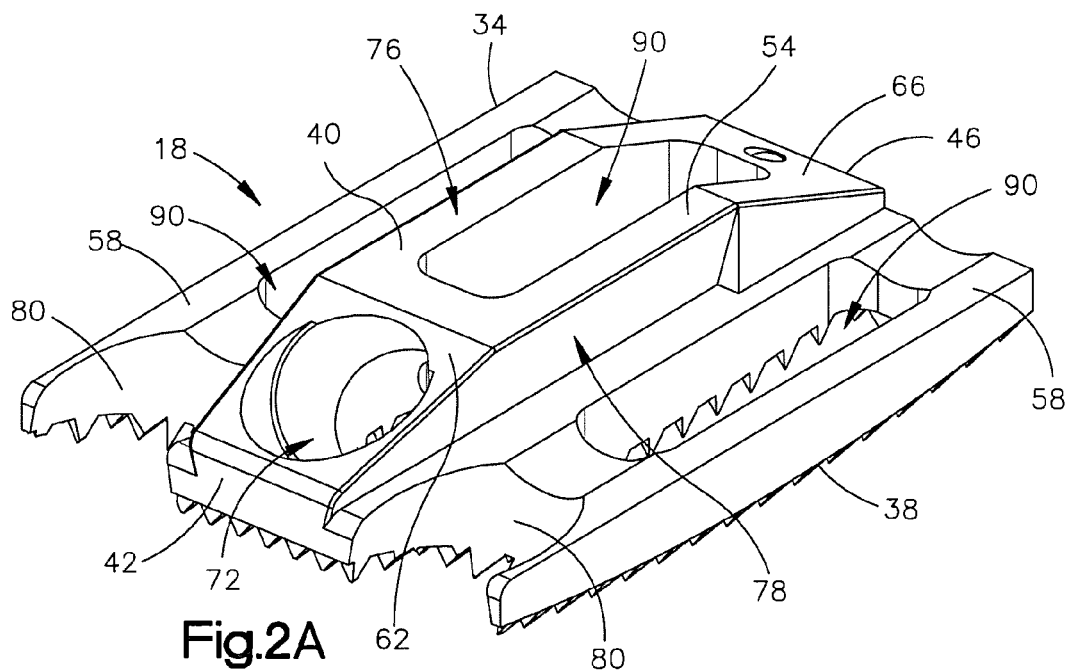
FIG. 2A is a front perspective view of the inferior implant body of the distractible fusion implant shown in FIG. 1B.
Figure 2B:
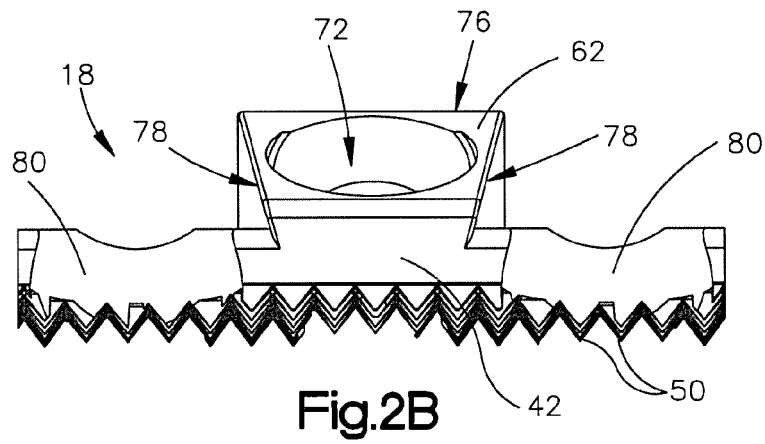
FIG. 2B is a front elevation view of the inferior implant body shown in FIG. 2A.
Figure 2C:
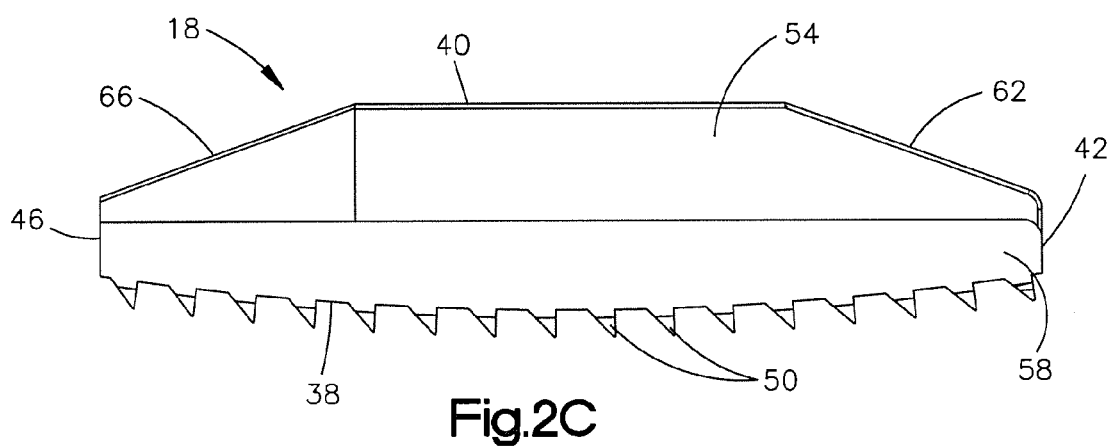
FIG. 2C is a side elevation view of the inferior implant body shown in FIG. 2A.

Referring to FIG. 1A, an intervertebral space 11 is defined between a superior vertebral body 12a and an inferior vertebral body 12b. The superior vertebral body 12a generally defines an inferior endplate 13a or superior surface of the intervertebral space 11, and the adjacent inferior vertebral body 12b defines a superior endplate 13b or inferior surface of the intervertebral space 11. Thus, the intervertebral space 11 is disposed between the vertebral bodies 12a and 12b. The vertebral bodies 12a and 12b can be anatomically adjacent vertebral bodies, or can remain after a discectomy has been performed that removed a vertebral body from a location between the vertebral bodies. As illustrated, the intervertebral space 11 is illustrated after a discectomy, whereby the disc material has been removed or at least partially removed to prepare the intervertebral space 11 to receive a disc implant that can achieve height restoration. The intervertebral space 11 can be disposed anywhere along the spine as desired. Moreover, the superior vertebral body 12a may be considered a first or a second vertebral body and the inferior vertebral body 12b may be considered a first or a second vertebral body.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

Referring also to FIG. 1B, an intervertebral implant, such as a distractable intervertebral implant 10, can be inserted into the intervertebral space 11 along a longitudinal insertion direction I, which can be a posterior direction in accordance with the illustrated embodiment or any other direction as desired. The distractable intervertebral implant 10 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the distractable intervertebral implant 10 is implanted into the intervertebral space 11 the transverse direction T extends generally along the superior-inferior (or caudal-cranial) direction, while the plane defined by the longitudinal direction L and lateral direction A lie generally in the anatomical plane defined by the anterior-posterior direction, and the medial-lateral direction. Accordingly, the directional terms "vertical" and "horizontal" are used to describe the distractable intervertebral implant 10 and its components as illustrated merely for the purposes of clarity and illustration.

Referring to FIG. 1B, the distractable intervertebral implant 10 includes a first or inferior implant body 18 and a second or superior implant body 14 that is coupled to the inferior implant body 18. The distractable intervertebral implant 10 can further include at least one first fixation member 22, illustrated as a first screw that couples the inferior implant body 18 to the inferior vertebral body 12b, and at least one second fixation member, such as second and third fixation members 26 and 30 illustrated as screws, that couple the superior implant body 14 to the superior vertebral body 12a. It should be understood that the fixation members 22, 26, and 30 may be also be configured as nails, blades, or graft. The distractable intervertebral implant 10 defines an anterior end 42 and an opposed posterior end 46. The anterior end 42 defines a trailing end of the distractable intervertebral implant 10 along the direction of insertion I, and the posterior end 46 defines a leading end of the distractable intervertebral implant 10 along the direction of insertion I.

The distractable intervertebral implant 10 may be partially or entirely formed from a metal, polymer, ceramic, allograft, or other artificial biomaterials such as beta-tricalcium phosphate. Suitable biocompatible materials or combinations of materials, may include PEEK, porous PEEK, carbon fiber-reinforced PEEK, titanium and titanium alloys, stainless steel, ceramic, polylactic acid, tantalum, magnesium, allograft, or other artificial biomaterials. The distractable intervertebral implant 10 presents an outer surface 19 that can be coated with any suitable material, such as hydroxyl apatite, beta-tricalcium phosphate, anodic plasma chemical treated titanium, or other similar coatings that improve osseointegration of the distractable intervertebral implant 10. As shown, the assembled implant 10 may be generally rectangular in shape, though it should be understood that all geometries are imaginable.

Referring to FIGS. 2A-2D the inferior implant body 18 includes a body portion 34 that defines a lower or inferior, or outer, engagement surface 38 configured to contact or otherwise face the superior endplate 13b of the inferior vertebral body 12b, an opposing inner surface 40, an anterior end 42, and an opposing posterior end 46. The body portion 34 further includes a plurality of engagement features 50, illustrated as teeth, that extend transversely out from engagement surface 38 and can be angled toward the anterior end 42 of the body portion 34. The engagement features 50 allow the inferior implant body 18 to easily translate along a posterior direction over the superior endplate of the inferior vertebral body during insertion of the inferior implant body 18 while at the same time provides immediate primary stability allowing the inferior implant body 18 to resist anterior migration. In other words, the engagement features 50 allow the inferior implant body 18 to easily slide in one direction, but if it were to slide in a second opposite direction, the teeth 50 would catch on the superior endplate 13b of the inferior vertebral body 12b to thereby prevent migration of the inferior implant body 18. It should be understood that the engagement features 50 can be shaped in any manner as desired, such as teeth, spikes, pyramids, cones, undefined geometries, rough surface topography, or independent bodies such a metal spikes that are embedded into the body portion 34 may be used.

Figure 2D:
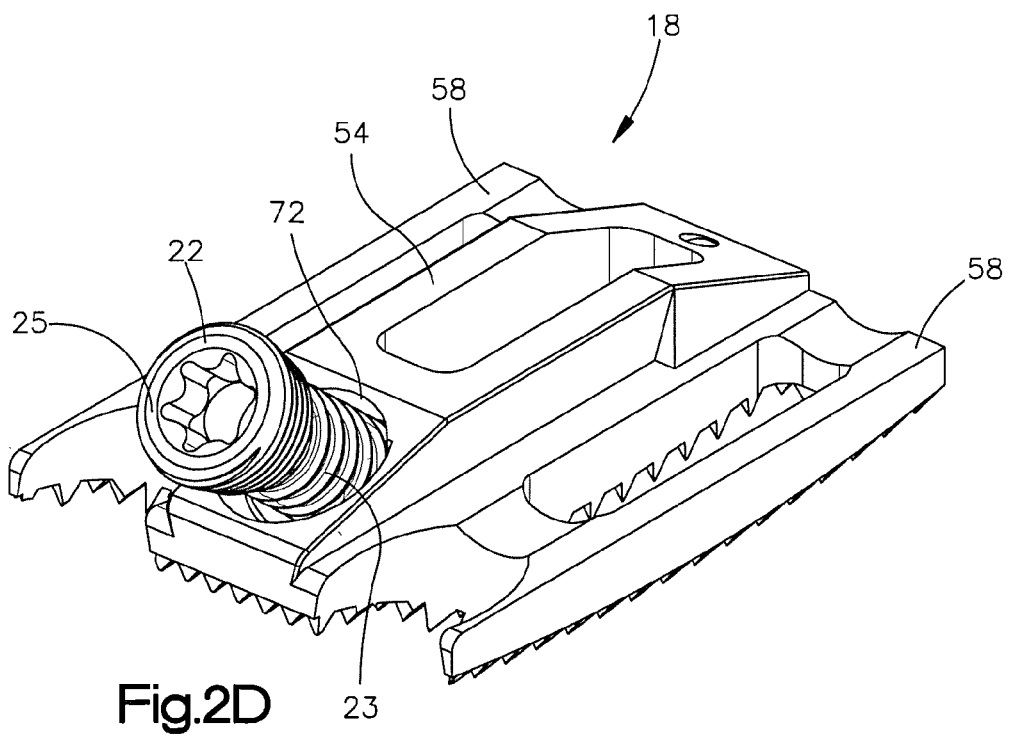
FIG. 2D is a front perspective view of the inferior implant body shown in FIG. 2A with a first fixation member being inserted into a bore of the inferior implant body.

As shown in FIGS. 2A-2D, the body portion 34, such as the inner surface 40, includes a middle region 54 and a first side region 58 extending from opposite sides of the middle region 54. The middle region 54 protrudes higher in the transverse vertical direction (or outwardly toward the superior implant body 14) with respect to the first side regions 58, and thus provides a longitudinally elongate rail that the superior implant body 14 can translate longitudinally along. In this way, the inner surface 40 of the body portion 34 defines the rail. In accordance with the illustrated embodiment, the anterior end 62 of the middle region 54 is angled upwards toward the superior implant body 14 as it extends toward the posterior end 46 of the body portion 34, and the posterior end 66 of the middle region 54 is angled upwards toward the superior implant body 14 as it extends toward the anterior end 42 of the body portion 34. As shown in FIG. 2A, the body portion 34 defines a bore 72 that extends through the anterior end 62. As shown in FIG. 2D, the bore 72 is configured to receive the first fixation member 22. The first fixation member 22 can include a shaft 23 and a head 25 that is dimensioned larger than the shaft 23. The bore 72 can likewise include a shaft-receiving region sized to receive the shaft 23, and a head receiving region sized to receive the head 25 when the fixation member 22 is fully received by the bore 72. The bore 72 can further be tapered and elongate along an angle toward the posterior end 46 of the body portion 34, such that the fixation member 22 is also elongate along the angle toward the posterior end 46 of the body portion 34 when received in the bore 72. The bore 72 can include a locking mechanism that engage a locking mechanism of the first fixation member 22, for instance a thread, a locking pin, a ratchet, a rough surface, etc. along one or both of the shaft 23 and the head 25. It should be understood that at least one or both of the shaft 23 and the head 25 can be substantially smooth and devoid of the locking mechanism. Likewise, at least one or both of the shaft-receiving region and the head-receiving region can be substantially smooth and devoid of the locking mechanism.

The middle region 54 further defines a top surface 76 and opposed side surfaces 78 that extend down from the top surface 76. The side surfaces 78 extend toward each other as they extend down from the top surface 76. That is, as the side surfaces 78 extend down from the top surface 76, the direction in which the side surfaces 78 extend includes a lateral component that extends toward the other side surface 78. Therefore, the side surfaces 78 and the top surface 76 define a dovetail shaped locking member. It should be understood, however, that the middle region may include configurations other than a dovetail shaped locking member. For example, the middle region may define an L-shaped locking member, a greater angulation longitudinal ratchet, etc.

As shown in FIG. 2A, the first side regions 58 include conical recesses 80 at their anterior ends. As shown, the conical recesses 80 are angled up as they extend toward the posterior end 46 of the body portion 34. As will be described later, the conical recesses 80 allow the second and third fixation members 26 and 30 to be inserted into the superior implant body 14 of the distractable intervertebral implant 10 at a specified angle.

The inferior implant body 18 can further include at least one graft window 90 such as a plurality of graft windows 90 that extend through at least one or more of the middle region 54 and the first side regions 58. Generally, each graft window 90 is elongate in the longitudinal direction, though it should be understood that any shape may be desired. The graft windows 90 are configured to receive autogenous bone graft or bone graft substitute such as Chronos, or DBM. For instance, the graft windows 90 may be pre-filled with the bone graft.

Referring to FIGS. 3A-3D, and 4A-4E the superior implant body 14 may be translated, for instance longitudinally, along the inferior implant body 18. As shown, the superior implant body 14 includes a body portion 134 that defines an upper or superior, or outer, engagement surface 138 configured to contact or otherwise face the inferior endplate 13a of the superior vertebral body 12a, an opposing interior surface 140, an anterior end 142, and an opposing posterior end 146. The body portion 134 further includes a plurality of engagement features 150 that extend transversely out from the engagement surface 138 and can be angled toward the anterior end 42 of the body portion 134. The engagement features 150 allow the superior implant body 14 to easily translate along a posterior direction under the inferior endplate of the superior vertebral body during insertion of the superior implant body 14 while at the same time provides immediate primary stability allowing the superior implant body 14 to resist anterior migration. In other words, the engagement features 150 allow the superior implant body 14 to easily slide in one direction, but if it were to slide in a second opposite direction, the engagement features 150 would catch on the inferior endplate 13a of the superior vertebral body 12a to thereby prevent migration of the superior implant body 14. It should be understood that the engagement features 150 can be shaped in any manner as desired, such as teeth, spikes, pyramids, cones, undefined geometries, rough surface topography, or independent bodies such a metal spikes that are embedded into the body portion 134 may be used.

As shown in FIGS. 3A-3D, the body portion 134, such as the inner surface 140, includes second side regions 154 that define a longitudinally elongate middle recess 158 configured to receive the longitudinally elongate rail of the body portion 34. The middle recess 158 extends into the body portion 134 from an inferior side of the superior implant body 14, and generally acts as a groove or channel that receives the middle region 54 of the inferior implant body 18. As shown, the middle recess 158 receives the middle region 54 of the inferior implant body 18 as the superior implant body 14 translates along the inferior implant body 18. An anterior end 162 of the middle recess 158 defines a conical recess 166 that is angled downwards. That is, the anterior end 162 of the middle recess 158 extends down as it extends toward the posterior end 146 of the body portion 134. Additionally, the anterior end 162 of the middle recess 158 defines a conical recess 166 that angles downward as it extends toward the posterior end 146 of the body portion 134. As will be described, the conical recess 166 enables the first fixation member 22 to be removed from the inferior implant body 18 of the distractable intervertebral implant 10 if so desired.

The middle recess 158 further defines a top surface 168 and opposing side surfaces 170 extending down from the top surface 168. The side surfaces 170 extend toward each other as they extend down from the top surface 168. That is, as the side surfaces 170 extend down from the top surface 168, the direction in which the side surfaces 170 extend includes a lateral component that extends toward the other side surface 170. Therefore, the side surfaces 170 and the top surface 168 define a dovetail shaped channel that receives the dovetail shaped middle region 54 of the inferior implant body 18. It should be understood, however, that the middle recess may include configurations other than a dovetail shaped channel. For example, the middle recess may define an L-shaped channel, a greater angulation longitudinal ratchet, etc.

Figure 3A:
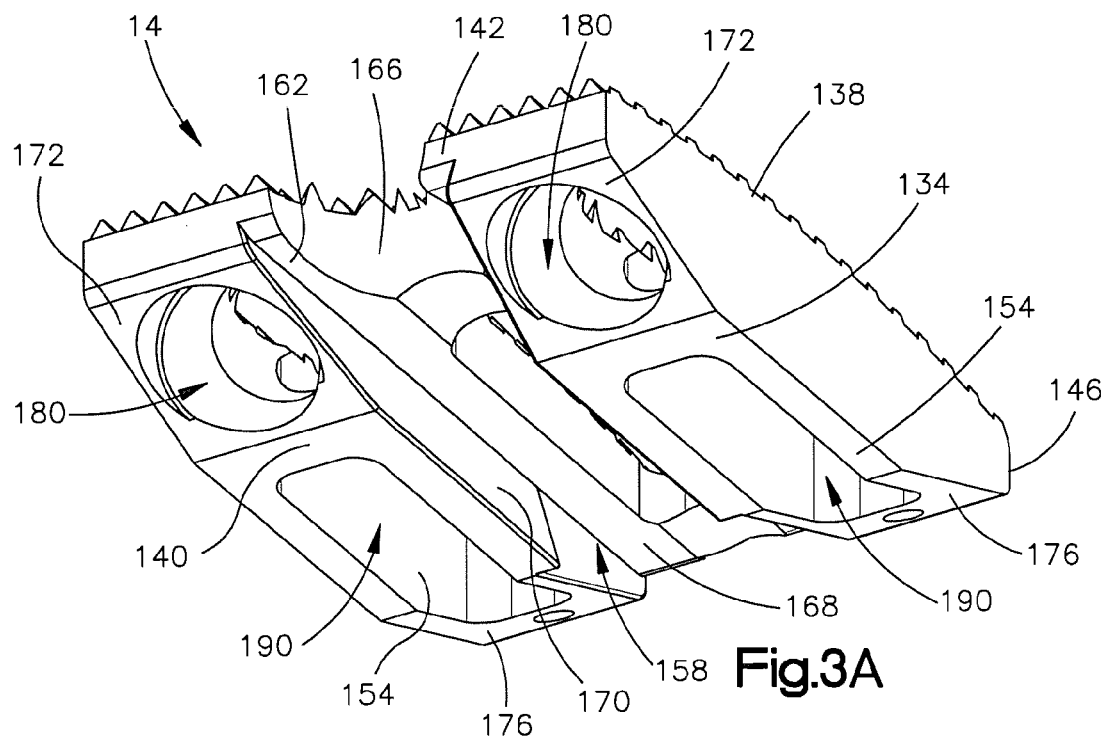
FIG. 3A is a bottom perspective view of the superior implant body of the distractible fusion implant shown in FIG. 1B.

The second side regions 154 each include an anterior end 172 and a posterior end 176 that are angled downwards. That is, the anterior end 172 of the second side regions 154 includes a surface that extend down or otherwise toward the inferior implant body 18 as they extend toward the posterior end 146 of the body portion 134, and the posterior end 176 of the second side regions 154 extend down or otherwise toward the inferior implant body 18 as they extend toward the anterior end 142 of the body portion 134. As shown in FIG. 3A, the body portion 134 defines a bore 180 that extends through each anterior end 172. As shown in FIG. 3D, each bore 180 is configured to receive one of the second and third fixation members 26 and 30. Like the first fixation member 22, the second and third fixation members can include a shaft 23 and a head 25 that is dimensioned larger than the shaft 23. The bores 180 can likewise include a shaft-receiving region sized to receive the shaft 23, and a head receiving region sized to receive the head 25 when the fixation members 26 and 30 are fully received by the bores 180. The bores 180 can further be tapered and elongate along an angle toward the posterior end 146 of the body portion 134, such that the fixation members 26 and 30 are also elongate along the angle toward the posterior end 146 of the body portion 134 when received in the bores 180. The bores 180 can include locking mechanisms that engage locking mechanisms of the second and third fixation members 26 and 30, for instance threads, locking pins, ratchets, rough surfaces, etc. along one or both of the shafts 23 and the heads 25. It should be understood that at least one or both of the shafts 23 and the heads 25 can be substantially smooth and devoid of the locking mechanisms. Likewise, at least one or both of the shaft-receiving regions and the head-receiving regions can be substantially smooth and devoid of the locking mechanisms.

As shown in FIGS. 3A and 3D, the superior implant body 14 can further include at least one graft window 190 such as a plurality of graft windows 190 that extend through at least one or more of the second side regions 154 as well as through the portion of the body portion 134 in which the recess 158 is defined. Generally, each graft window 190 is elongate in the longitudinal direction, though it should be understood that any shape may be desired. The graft windows 190 are configured to receive autogenous bone graft or bone graft substitute such as Chronos, or DBM. For instance, the graft windows 190 may be pre-filled with the bone graft.

As shown in FIG. 3D, the second and third fixation members 26 and 30 may be inserted into the bores 180 of the superior implant body 14 once the superior implant body 14 is fully slid onto the inferior implant body 18. The second and third fixation members 26 and 30 extend at an angle toward the posterior end of the distractable intervertebral implant 10. The second and third fixation members 26 and 30 engage the inferior endplate of the superior vertebral body to thereby securely attach the distractable intervertebral implant 10 to the superior vertebral body.

As shown in FIGS. 4A-4E, when the superior implant body 14 is fully slid onto the inferior implant body 18, the graft windows 190 of the superior implant body 14 align with the graft windows 90 of the inferior implant body 18. Therefore, the graft windows 90 and 190 define transverse channels that extend through the assembled implant 10. The graft windows 190 may be pre-filled with the bone graft.

As shown in FIGS. 4A-4D, the superior implant body 14 lockingly engages the inferior implant body 18 with respect to at least one or both of relative rotation and relative translation along a direction angularly offset with respect to the longitudinal insertion direction I when the recess 158 of the superior implant body 14 has received the rail of the inferior implant body 18. In that regard, the dovetail shaped recess 158 of the superior implant body 14 engages the dovetail shaped middle region 54 of the inferior implant body 18 when the inferior implant body 18 is received by the superior implant body 14 to create a form fit between the superior and inferior implant bodies 14 and 18. This form fit eliminates rotational degrees of freedom between the superior and inferior implant bodies 14 and 18. Other interlocking features between the superior implant body 14 and the inferior implant body 18 are envisioned to prevent translation in the longitudinal direction, such as a snap-action mechanism (e.g. PE-inlay or Prodisc-L). A third body (e.g. splint, pin, screw, bolt, glue) that is inserted after intraoperative assembly of the superior and inferior implant bodies 14 and 18 may also be used.

Figure 4C:
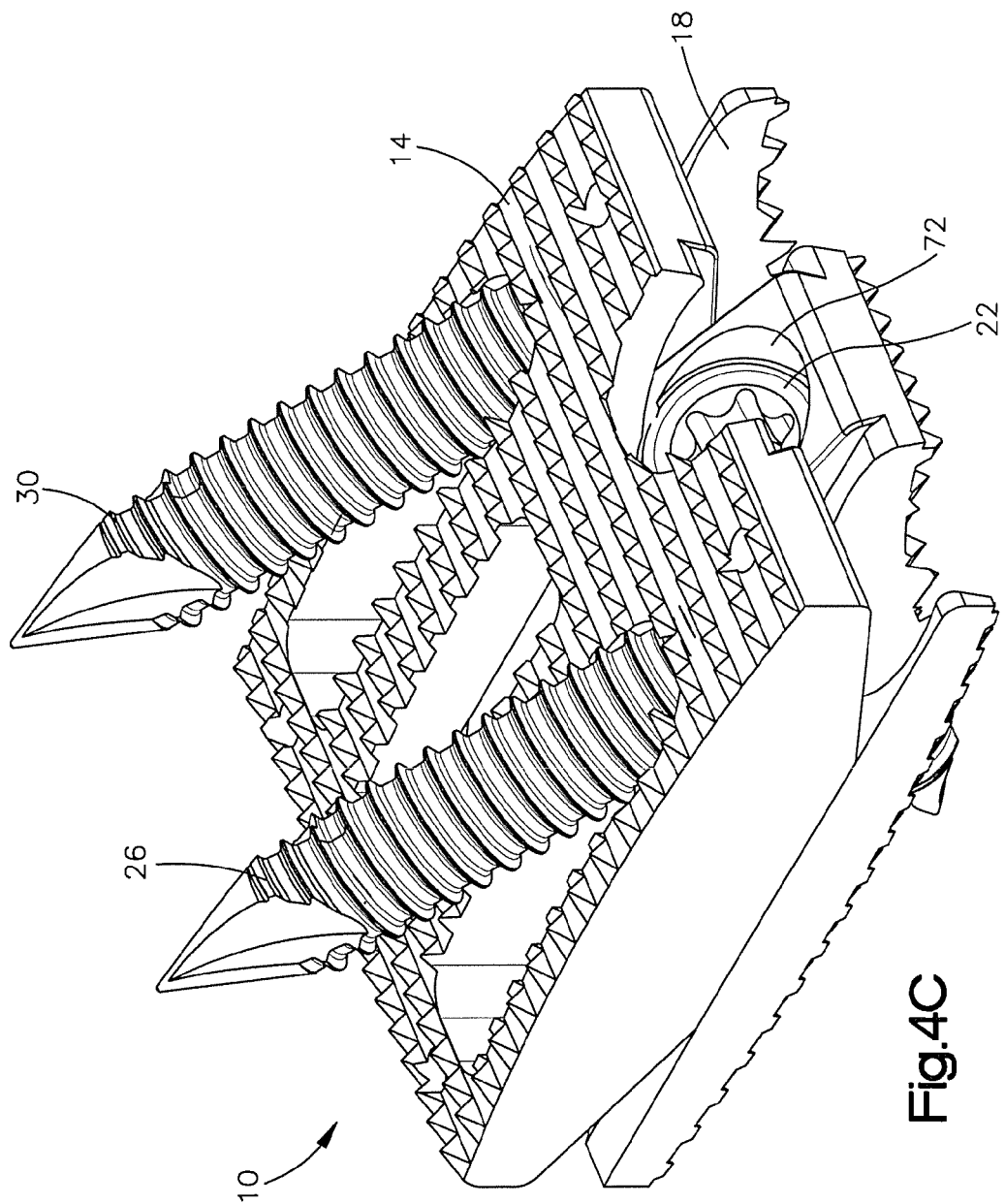
FIG. 4C is a front perspective view of the implant shown in FIG. 4B with three locking screws received within the bores of the superior and inferior implant bodies.
Figure 4D:
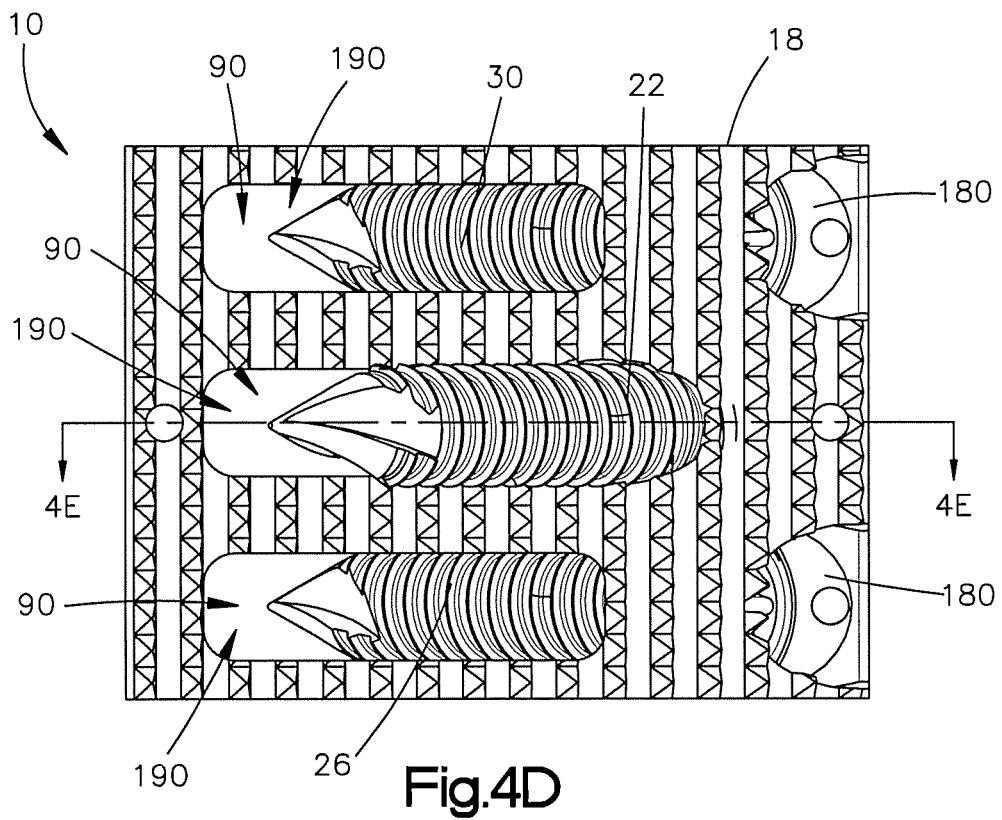
FIG. 4D is a top plan view of the implant shown in FIG. 4C.
Figure 4E:
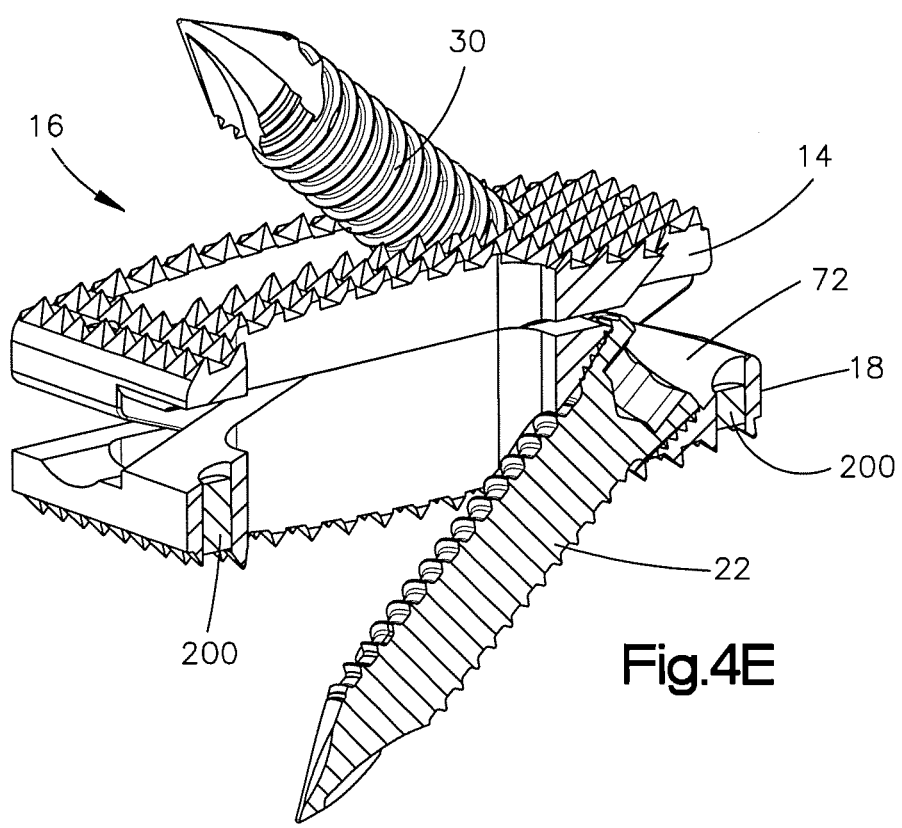
FIG. 4E is a cross-sectional view of the implant shown in FIG. 4D through the line 4E-4E.

As shown in FIGS. 4C-4E, the bores 72 and 180 are conical in shape. The conical shaped bores 72, 180 are configured to prevent the fixation members 22, 26, and 30 from being over inserted into the bores, and allow for angle stable fixation. The angle stable fixation prevents the fixation members not only from being over inserted but also from backing out. Thus, as each bore 72 and 180 receives its respective fixation members 22, 26, and 30 the heads of the fixation members 22, 26, and 30 will eventually abut the walls of the bores 72 and 180 to thereby prevent further insertion of the fixation members 22, 26, and 30. Such a configuration allows for a more stable fixation of the fixation members 22, 26, and 30. Furthermore, the angle stable connection between the fixation member's head and its counter part allow it to bear a bending moment.

As shown in FIG. 4E, the distractable intervertebral implant 10 may include marker pins 200, which may be used in case of a radiolucent base material that would not be visible in fluoroscopy/x-ray equipment. As shown, marker pins 200 may be buried within the body portion 34 of the inferior implant body 18. The marker pins 200 may be radioopaque to allow easy identification of the distractable intervertebral implant 10 in fluroscopique images. It should be understood that the implant 10 may include any number of pins 200, and that the pins 200 may also be buried within the superior implant body 14. Furthermore, instead of radiopaque marker pins 200, it may be possible to use polymers, ceramics, or biomaterials that include barium sulfate, or a similar substance. Barium sulfate (that is either homogeneously or inhomegeneously distributed in the base material) allows to make a radiopaque base material visible under fluoroscopy/x-ray equipment.

Figure 5B:
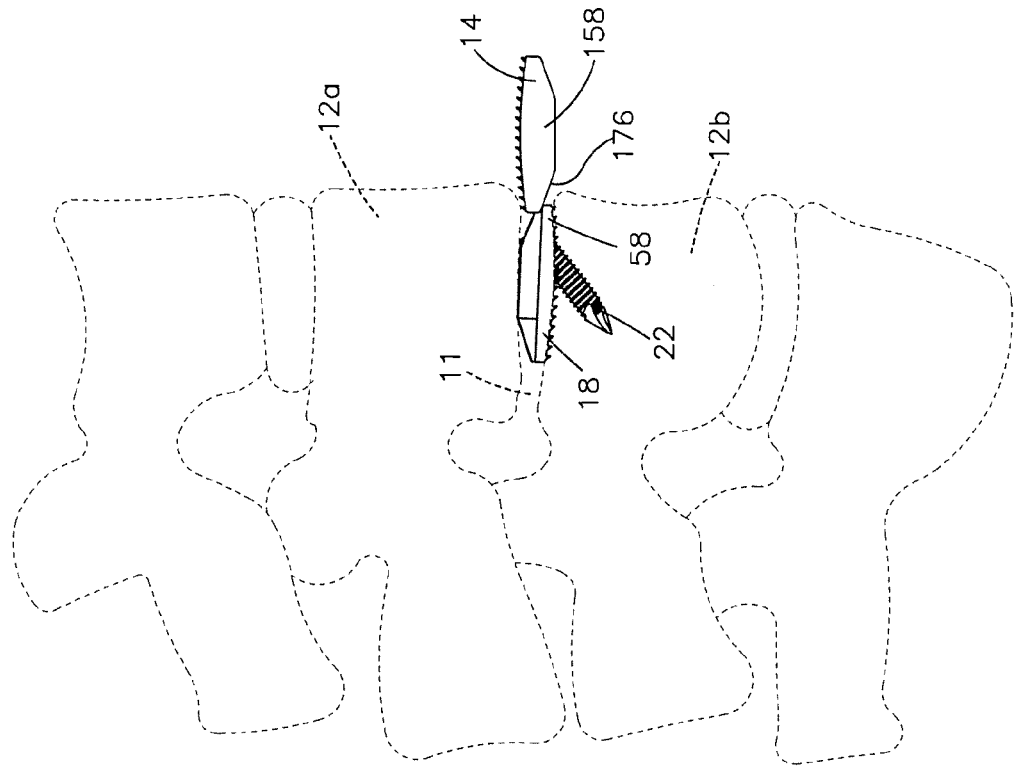
FIG. 5B is a side elevation view of the inferior implant body affixed to the inferior vertebral body with a first fixation member and a ramp portion of the superior implant body contacting an edge of the inferior implant body as it is being slid onto the intervertebral space.
Figure 5A:
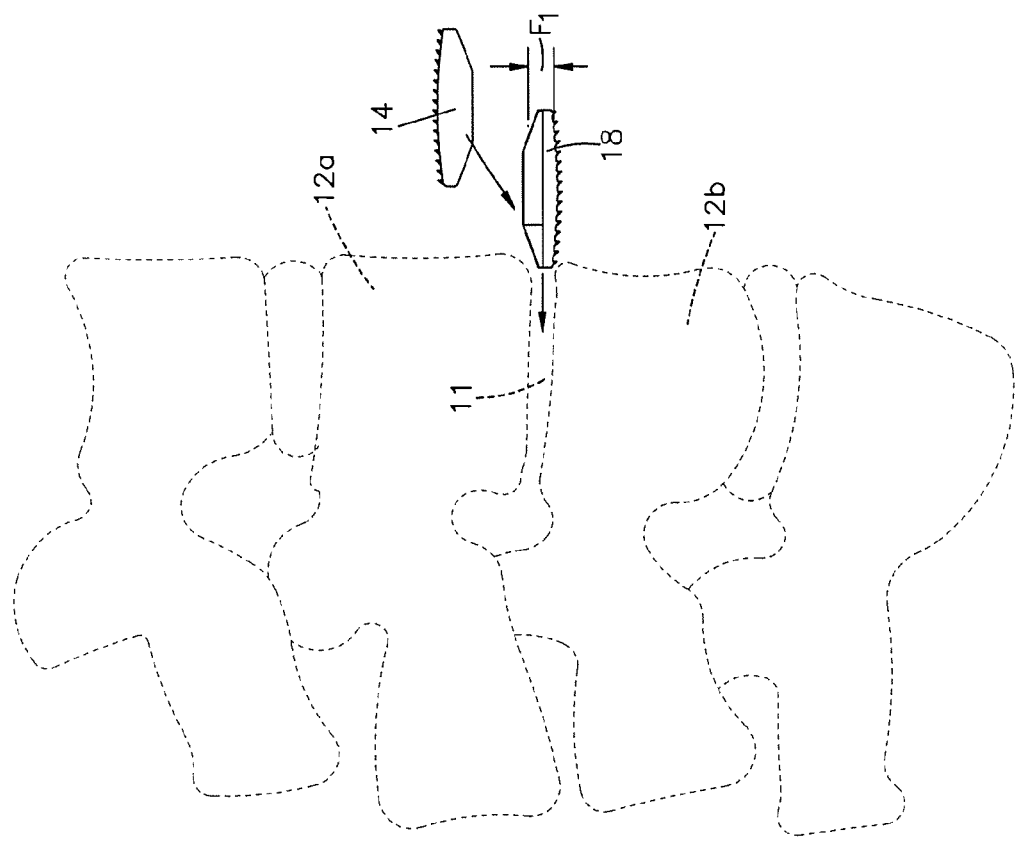
FIG. 5A is a side elevation view of the inferior implant body being slid into the intervertebral space defined between the superior and inferior vertebral bodies to thereby partially distract the vertebral bodies away from each other.

As shown in FIGS. 5A-5D, both the inferior implant body 18 and the superior implant body 14 may act as distractors as they are individually slid into the intervertebral space 11. As shown, in FIG. 5A, as the inferior implant body 18 is positioned within the intervertebral space 11 at least one of the superior vertebral body 12a and the inferior vertebral body 12b moves away from the other such that the superior and inferior vertebral bodies are separated by a first distance $F_1$. The first distance $F_1$ may be substantially equal to the transverse height of the inferior implant body 18. Once the inferior implant body 18 is properly positioned and attached to the inferior vertebral body 12b, the superior implant body 14 may be slid or otherwise translated over the inferior implant body 18 and into the intervertebral space 11. As shown in FIG. 5B, the angled posterior ends 176 of the superior implant body's second side regions 154 contact respective second side regions 58 of the inferior implant body 18. Because of the angled posterior ends 176 of the superior implant body 14, the superior implant body 14 will move toward the superior vertebral body 12a as the superior implant body 14 is slid over the inferior implant body 18, as shown in FIGS. 5B-5D to thereby cause at least one of the superior vertebral body 12a and the inferior vertebral body 12b to move away from the other such that the vertebral bodies are separated by a second distance $F_2$ that is greater than the first distance $F_1$. In this way, continuous distraction is achieved until the superior implant body 14 is fully assembled with the inferior implant body 18. As shown in FIG. 5D, the superior implant body 14 may move a distance H in an upward direction once it has been fully slid onto the inferior implant body 18. The distance H as well as the degree of distraction may depend on the angle at which the posterior ends 176 extend toward the anterior end of the superior implant body 14.

In operation, the inferior implant body 18 is first inserted into the intervertebral space. Once properly placed, the first fixation member 22 may be inserted into the bore 72 of the inferior implant body 18 and driven into the inferior vertebral body. Next the superior implant body 14 is pushed into the intervertebral space or otherwise slid over the inferior implant body 18. During insertion of the superior implant body 14, the superior implant body 14 slides over the inferior implant body 18. As described in relation to FIGS. 5A-5D, as the superior implant body 14 is sliding onto the inferior implant body 18, the superior implant body 14 moves up toward the superior vertebral body. Therefore, a continuous distraction of the inferior and superior vertebral bodies is achieved until the distractable intervertebral implant 10 is fully assembled. The superior implant body 14 interlocks with the inferior implant body 18 and builds a solid construct. The assembled implant 10 withstands translation and rotation in all six degrees of freedom.

Once the assembled implant 10 is properly positioned, the second and third fixation members 26 and 30 may be inserted into the bores 180 of the superior implant body 14. The second and third fixation members 26 and 30 engage the inferior endplate of the superior vertebral body to thereby securely attach the superior implant body 14 and therefore the distractable intervertebral implant 10 to the superior vertebral body.

Because the distractable intervertebral implant 10 may be placed into the intervertebral space 11 by first inserting the inferior implant body 18 and then the superior implant body 14, the distractable intervertebral implant 10 may be inserted into the intervertebral space 11 either from the anterior end of the patient or from the posterior end of the patient. In other words, by positioning the distractable intervertebral implant 10 in pieces rather than as a fully assembled construct the surgeon will be capable of accessing the intervertebral space 11 from the posterior end of the patient which is usually difficult, due to the limited amount of space. It should be understood that any surgical approach (i.e. anterior, anterolateral, lateral, extraforaminal, transforaminal, and posterior) may be considered.

It should be appreciated that the distractable intervertebral implant 10 described herein can be configured so as to provide a range of numerous possible geometries and angular relationships. For example, while the superior implant body 14 is described as having angled posterior ends that cause the superior implant body 14 to move upwards and thereby act as a distractor, it is possible to include an angled anterior end on the inferior implant body 18 to cause the superior implant body 14 to distract as it is inserted. Furthermore, it is envisioned that the superior implant body 14 could be inserted into the intervertebral space prior to the insertion of the inferior implant body 18.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure.

What is claimed:

1. A method for inserting an intervertebral implant into an intervertebral disc space that is defined between a first vertebral body and a second vertebral body that is spaced from the first vertebral body along a vertical direction, the method comprising:
    inserting a first implant body into the intervertebral space so as to cause at least one of the first and second vertebral bodies to move away from the other of the first and second vertebral bodies, the first implant body including an outer surface that faces the first vertebral body, and an inner surface opposite the outer surface; and
    inserting a second implant body into the intervertebral space such that an outer surface of the second implant body that faces the second vertebral body moves away from the outer surface of the first implant body as an inner surface of the second implant body is translated over the inner surface of the first implant body, the second implant body causing at least one of the first and second vertebral bodies to move further away from the other as the second implant body is being inserted.

2. The method according to claim 1, further comprising the step of inserting a fixation member through a bore of the first implant body and into the first vertebral body to thereby affix the first implant body to the first vertebral body.

3. The method according to claim 2, wherein the step of inserting the fixation member comprises affixing the first implant body to the first vertebral body prior the second implant body being inserted.

4. The method according to claim 3, further comprising the step of inserting a second fixation member and a third fixation member through the second implant body and into the second vertebral body to thereby affix the second implant body to the second vertebral body.

5. The method according to claim 1, further comprising the step of mating the inner surface of the second implant body with the inner surface of the first implant body to thereby interlock the first and second implant bodies such that no other implant bodies can be inserted between the first and second implant bodies.

6. The method according to claim 1, wherein the inner surface of one of the first implant body and the second implant body defines a rail and the inner surface of the other of the first implant body and second implant body defines a recess configured to receive the rail, and wherein the second inserting step comprises inserting the second implant body such that the recess receives the rail.

7. The method according to claim 1, wherein the second inserting step comprises translating the second implant body over an angled trailing end of the first implant body.

8. The method according to claim 7, wherein the second inserting step further comprises translating the second implant body such that an angled leading end of the second implant body contacts a side region of the first implant body.

9. The method according to claim 1, wherein the intervertebral implant is devoid of a third implant body.

10. A method for inserting an intervertebral implant into an intervertebral disc space that is defined between a first vertebral body and a second vertebral body that is spaced from the first vertebral body along a vertical direction, the method comprising:

inserting a first implant body into the intervertebral space so as to cause at least one of the first and second vertebral bodies to move away from the other of the first and second vertebral bodies, the first implant body including an angled trailing end; and inserting a second implant body into the intervertebral space such that the second implant body contacts the angled trailing end and translates along the angled trailing end to thereby cause at least one of the first implant body and the second implant body to move along the vertical direction, the second implant body causing at least one of the first and second vertebral bodies to move further away from the other as the second implant body is being inserted.

11. The method according to claim 10, further comprising the step of inserting a fixation member through a bore of the first implant body and into the first vertebral body to thereby affix the first implant body to the first vertebral body.

12. The method according to claim 11, wherein the step of inserting the fixation member comprises affixing the first implant body to the first vertebral body prior the second implant body being inserted.

13. The method according to claim 12, further comprising the step of inserting a second fixation member through the second implant body and into the second vertebral body to thereby affix the second implant body to the second vertebral body.

14. The method according to claim 13, further comprising the step of inserting a third fixation number through the second implant body and into the second vertebral body.

15. The method according to claim 10, further comprising the step of mating an inner surface of the second implant body with an inner surface of the first implant body to thereby interlock the first and second implant bodies such that no other implant bodies can be inserted between the first and second implant bodies.

16. The method according to claim 10, wherein the second inserting step comprises causing an angled leading end of the second implant body to contact a side region of the first implant body.

17. The method according to claim 10, further comprising the step of interlocking the first and second implant bodies such that the assembled implant withstands translation and rotation in all six degrees of freedom.

18. A method for inserting an intervertebral implant into an intervertebral disc space that is defined between a first vertebral body and a second vertebral body that is spaced from the first vertebral body along a vertical direction, the method comprising:

inserting a first implant body into the intervertebral space;

inserting a first fixation member through the first implant body and into the first vertebral body to thereby affix the first implant body to the first vertebral body;

inserting a second implant body into the intervertebral space after affixing the first implant body to the first vertebral body such that the second implant body translates over the first implant body to thereby cause at least one of the first and second vertebral bodies to move away from the other; and inserting a second fixation member through the second implant body and into the second vertebral body to thereby affix the second implant body to the second vertebral body.

19. The method according to claim 18, further comprising the step of inserting a third fixation member through the second implant body and into the second vertebral body.

20. The method according to claim 18, wherein inserting the second implant body comprises translating the second implant body over the first implant body so as to move an outer surface of the second implant body away from an outer surface of the first implant body.

21. The method according to claim 18, wherein inserting the first fixation member comprises inserting the first fixation member through an angled trailing end of the first implant body.

22. The method according to claim 21, wherein inserting the second implant body comprises translating the second implant body along the angled trailing end of the first implant body such that the angled trailing end causes an outer surface of the second implant body to move away from an outer surface of the first implant body.

23. The according to claim 22, wherein inserting the second fixation member comprises inserting the second fixation member through an angled trailing end of the second implant body.

\* \* \* \* \*